United States Patent [19]
Yamagishi et al.

[11] Patent Number: 5,331,287
[45] Date of Patent: Jul. 19, 1994

[54] DEVICE AND METHOD FOR SENSING WATER AND/OR ACID IN THE PRESENCE OF WATER IN NON-AQUEOUS MEDIA

[75] Inventors: Frederick G. Yamagishi; Camille Van Ast, both of Newbury Park; Leroy J. Miller, West Hills, all of Calif.

[73] Assignee: Hughes Aircraft Company, Los Angeles, Calif.

[21] Appl. No.: 922,899

[22] Filed: Jul. 31, 1992

[51] Int. Cl.$^5$ .................... G01N 27/02; G01N 27/30; G01R 27/00
[52] U.S. Cl. .................................. 324/724; 324/446; 324/694; 204/421; 73/61.44; 340/438; 340/603
[58] Field of Search ............... 324/439, 446, 693, 694, 324/698, 722, 724; 204/421; 73/53.04, 61.44; 340/602, 604, 438, 603

[56] References Cited

U.S. PATENT DOCUMENTS

| | | | |
|---|---|---|---|
| 3,710,237 | 1/1973 | Watson et al. | 324/446 |
| 4,455,530 | 6/1984 | Lee et al. | 324/446 |
| 4,791,374 | 12/1988 | Yodice et al. | 324/439 |
| 5,023,133 | 6/1991 | Yodice et al. | |
| 5,027,077 | 6/1991 | Yamagisawa et al. | 324/694 X |
| 5,089,780 | 2/1992 | Megerle | |

FOREIGN PATENT DOCUMENTS

| | | |
|---|---|---|
| 0442314 | 8/1991 | European Pat. Off. |
| 0442314A2 | 8/1991 | European Pat. Off. |

OTHER PUBLICATIONS

Database WPI, Week 8445, Sep. 20, 1984, Derwent Publications Ltd., London, GB AN 84-276262 & AU-2 583 884 (Warman Int Ltd) Sep. 20, 1984.

J. Physl. Chem. 1985, 89, 1441-1447, "Resistance of Polyaniline Films as a Function of Electrochemical Potential and the Fabrication of Polyaniline-Based Microelectronic Devices", E. Paul, et al. (no month).

Synthetic Metals, 13, 1986, 193-205, 'Polyaniline': Protonic Acid Doping of the Emeraldine Form to the Metallic Regime, J. Chiang et al. (no month).

Primary Examiner—Gerard R. Strecker
Assistant Examiner—Diep Do
Attorney, Agent, or Firm—V. D. Duraiswamy; W. K. Denson-Low

[57] ABSTRACT

A sensor for monitoring the water content and the acid content in the presence of water in nonaqueous media can be incorporated into a monitoring system for monitoring the quality of nonaqueous fluids in equipment or vehicles. The sensor comprises an insulating substrate; electrodes formed on the substrate in an interdigitated pattern; and a conductive polymer deposited over the interdigitated electrodes which bridges between adjacent digits of the electrodes. The monitoring system incorporating the sensor comprises a control module for measuring the conductivity of the sensor. The control module is preprogrammed to compare the measured conductivity to a predetermined level indicative of an unacceptable level of degradation. The sensor is made by depositing electrodes on an insulating substrate; depositing a conductive polymer over the electrodes in an amount sufficient to bridge between the electrodes; and neutralizing the conductive polymer to an insulating form. A method of sensing water and acid in the presence of water in nonaqueous media exposes an insulating form of a conductive polymer to a nonaqueous medium and monitors the conductivity of said conductive polymer, as the nonaqueous medium is used. The conductive polymer reversibly increases conductivity in measurable amounts with increasing acid and/or water content due to protonation by the acid or hydration by the water.

17 Claims, 4 Drawing Sheets

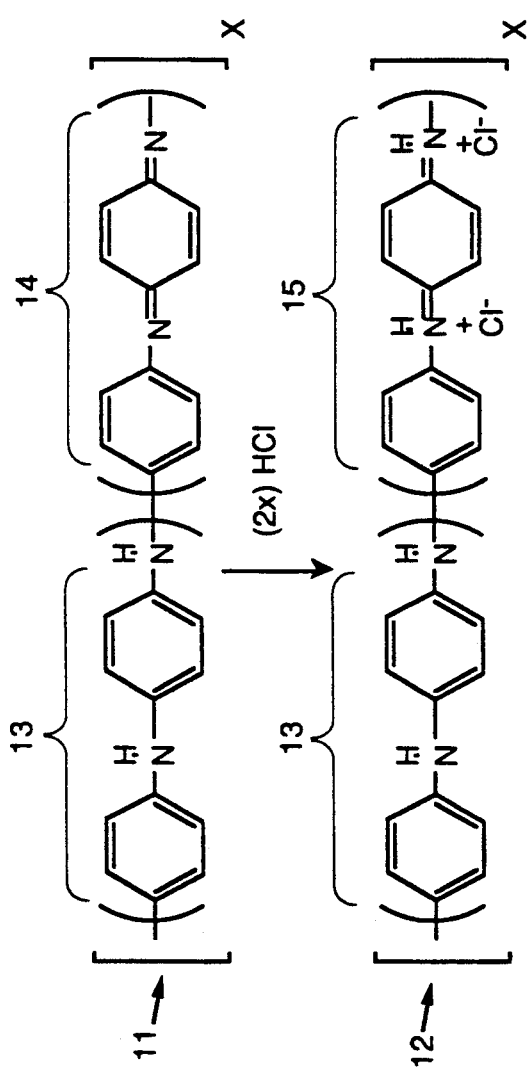
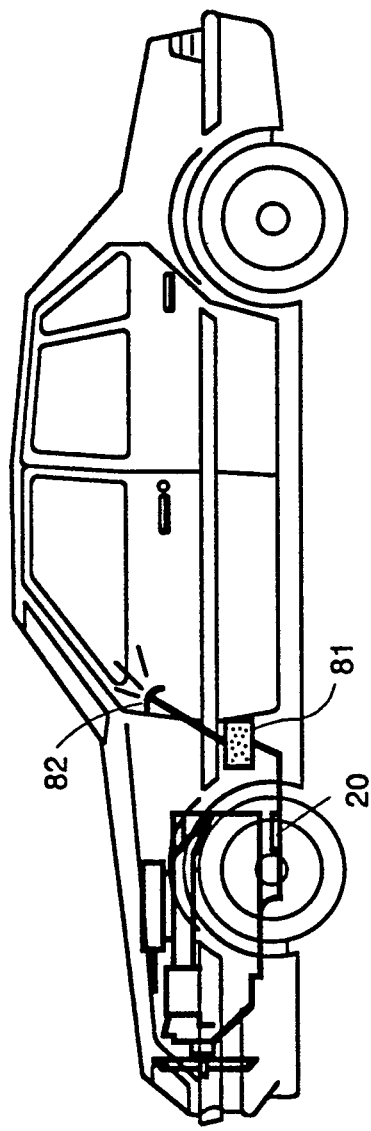
FIG.1.
FIG.8.

DEVICE AND METHOD FOR SENSING WATER AND/OR ACID IN THE PRESENCE OF WATER IN NON-AQUEOUS MEDIA

BACKGROUND OF THE INVENTION

1. Field of the Invention

The present invention relates to measuring the acid and/or water content of nonaqueous media and measuring the acid content in the presence of water of such nonaqueous media. In particular, the present invention relates to monitoring the quality or condition of engine oil.

2. Description of the Related Art

Acid species in nonaqueous media, such as hydrocarbon-based oil, cause gelling and change the viscosity of the oil so that there is an overall loss of lubricity. Oil in an engine, for example, containing an acid species will not properly coat the engine's moving parts causing the parts to seize up and prematurely fail. Moreover, acid species in hydrocarbon-based oil causes corrosion of the engine's metallic parts.

Water accumulation in engine oil is problematic also. Depending on the geographic region and seasonal weather conditions, water may accumulate in the engine oil faster than it is evaporated. Prolonged exposure of the engine's moving parts to accumulated water will cause corrosion. Moreover, accumulated water in engine oil will remove oil additives and preservatives, which function to neutralize acid species.

The quality of oil is particularly important in the automotive industry. Automobile manufacturers recommend that a vehicle's oil be replaced on a regular basis based on the number of miles the vehicle has been driven. Typically, the actual condition of the oil at the time it is replaced is not known. If the oil should degrade prematurely, the vehicle is operated with the degraded oil at least until the next regularly scheduled oil change. On the other hand, if the vehicle is operated under much less rigorous conditions, including weather conditions, or conditions that are favorable to an extended lifetime for the oil, the oil may be replaced and discarded prematurely, which increases the cost of operation and causes unnecessary environmental problems. With respect to water accumulation, a vehicle driven in a cold winter climate for only a few miles a day, will accumulate water in the engine oil to a much greater extent than a vehicle driven in a warmer climate. Nevertheless, the recommended schedule for changing the oil in the vehicle is the same.

Other important areas of application include diesel engines and automatic transmission fluids. In the former case, diesel fuel contains significant amounts of organosulfur compounds, which degrade through use and are oxidized eventually to sulfuric acid. Not only is sulfuric acid highly corrosive, but it causes increased operating temperatures of the oil. Automatic transmission fluids are also hydrocarbon-based materials and they thermally oxidize to carboxylic acids leading to similar eventual operating problems.

It would be desirable if the engine oil in a vehicle could be monitored and replaced only when the oil has degraded to a level which is rated unacceptable to the proper operation of a vehicle.

One monitoring device for indicating when oil has degraded to an unacceptable level is known from U.S. Pat. No. 5,089,780 issued to Megerle on Feb. 18, 1992. Megerle discloses a sensor and system for monitoring the accumulation of contaminants in oil. The contaminants must have an electrical conductivity which is different from the oil. An alternating current conductivity is measured by an electrochemical cell and an indication of the amount of the contaminants present is provided. The conductivity cell includes concentric cylindrical electrodes mounted on a plug or other structure so that they can be immersed in the engine oil. The plug can be mounted in the oil sump, or oil stream, of the engine. One electrode is connected to an AC conductivity measuring device which is connected to a warning light or display device that provides an indication of the oil conductivity. The ability and usefulness of the Megerle device for monitoring the accumulation of water is not known. Moreover, contaminants dissolved in accumulated water in the oil are less likely to be detected with an electrochemical cell.

Conductive polymers have been used as the active material in sensors to detect acidity, or more specifically, pH in aqueous and highly polar systems. Conductive polymer acidity sensors are advantageous because they are compact, simple, inexpensive, and easy to make. A number of high sensitivity prototype sensing devices have been reported using the conductive polymer, polyaniline, as the active sensing material. For example see J-C. Chiang and A. G. MacDiarmid, Synth. Met., Vol. 13, 193 (1986). These range from chemical gas sensors to pH sensors in aqueous solutions.

Yodice et al., U.S. Pat. No. 5,023,133 issued Jun. 11, 1991, discloses an acid sensing device for nonaqueous media, such as motor vehicle lubricating oil. The devices comprise an organic polymer, such as polyaniline or polypyrrole, which is capable of accepting protons. However, Yodice et al. are silent with respect to the ability to monitor water content and acid content in the presence of water.

Y. Maeda, European Patent Application No. 0 442 314 A2, published Aug. 21, 1991, disclose an apparatus for detecting deterioration of lubricating oil. The apparatus comprises a membrane of polyaniline which is treated with an electrical oxidation and an electrical reduction that is immersed in lubricating oil. The electrical resistance of the membrane changes with changes in the amount of acid in the deteriorating lubricating oil. The deterioration is monitored by measuring the electrical resistance between a pair of electrodes.

Maeda et al., like Yodice et al., are silent with respect to a device which comprises a conductive polymer for accurately monitoring water content and acid content in the presence of water in such nonaqueous media.

Therefore, there is a need for a compact, low cost sensor having a conductive polymer as the active element that is adaptable for a method of monitoring acid content, water content, and/or acid content in the presence of water in nonaqueous and nonpolar media, such as hydrocarbon-based oil.

SUMMARY OF THE INVENTION

In accordance with the invention, the electrical conductivity of a conductive polymer can be changed by hydration with water, as well as, by protonation with acids in nonaqueous media. Moreover, the acid content in the presence of water can be accurately measured. A sensor and monitoring system for sensing the acid and/or water content and the acid content in the presence of water in nonaqueous media and a method of making the sensor are provided which use a conductive polymer as the active sensing material to monitor the concentration of acid and/or water in nonaqueous or nonpolar media. The conductive polymer reversibly changes conductivity in measurable amounts with changes in the acid and/or water content. The invention is particularly suited for nonaqueous, nonpolar or nonionizing media, such as hydrocarbon-based oil or other fluids, such as transmission fluid.

A method of sensing acid and/or water content and acid in the presence of water in nonaqueous media is provided which monitors the conductivity of the conductive polymer during exposure to the nonaqueous medium. The sensing devices, monitoring system and methods provide an electronic means for monitoring a nonaqueous or nonpolar medium for changes in acid and/or water concentration levels, because the conductive polymer reversibly changes conductivity depending on the degree of protonation and/or hydration. Protonation and hydration occurs by the movement of charge via the movement of electrons through the film, in contrast to the electrochemical migration of ions in an electrochemical cell sensor of the prior art.

The sensors for monitoring acid and/or water content and acid in the presence of water in nonaqueous or nonpolar media comprises an insulating substrate; electrodes formed on the substrate in an interdigitated pattern; and a conductive polymer deposited over the interdigitated electrodes in an amount sufficient to bridge between adjacent digits of the electrodes, which reversibly increases in conductivity due to protonation or hydration.

The method of sensing acid and/or water content and acid content in the presence of water in nonaqueous media comprises the steps of exposing an insulating form of a conductive polymer, which changes conductivity by protonation or hydration, to a nonaqueous medium and monitoring the conductivity of said conductive polymer, as the nonaqueous medium is used.

A method of making a sensor for monitoring the acid and/or water content and acid content in the presence of water in nonaqueous media comprises the steps of depositing electrodes on an insulating substrate in an interdigitated pattern; electrochemically depositing a conductive polymer, which changes conductivity due to protonation or hydration, over the interdigitated electrodes as a thin film in an amount sufficient to bridge between adjacent digits of the electrodes; and neutralizing the conductive polymer to an insulating form. The conductive polymer is selected from the group consisting of polyaniline and the alkyl- and alkoxy-substituted derivatives thereof, which change conductivity due to protonation or hydration.

In one embodiment, the sensing device is installed in vehicles, such as automobiles, trucks, buses and other heavy equipment and stationary equipment, such as vacuum pumps, to monitor the condition of motor oil, transmission fluid and other nonaqueous media used therein. The device is mounted to be exposed to the nonaqueous medium. For example, the sensor can be welded into the motor oil pan or incorporated into the motor oil drain plug to monitor the motor oil or welded into the transmission fluid reservoir to monitor the transmission fluid. The electrodes of the sensor are interconnected with a control means, such as a vehicle's engine control module (ECM). The ECM monitors the conductivity of the sensor and is pre-programmed to display a warning in the form of a light or audio signal to the operator of the equipment when the conductivity reaches a certain predetermined level that corresponds to an unacceptable acid and/or water content in the medium. When an unacceptable degradation level is reached, the ECM incorporating the invention provides notification to the operator that the particular nonaqueous medium should be changed. The monitoring system according to the invention comprises a sensor having interdigitated electrodes on an insulating substrate and a conductive polymer deposited over the interdigitated portion of the electrodes in an amount sufficient to bridge between adjacent digits. The conductive polymer reversibly increases in conductivity due to hydration by water or by protonation acid species derived from degradation of the nonaqueous medium.

A real-time continuous sensing device and electronic method of monitoring the quality of motor oil can decrease warranty expenses related to degraded oil, which are estimated to be about $11 to $15 per automobile and much higher for large trucks and heavy-equipment. Currently, there are no real-time sensors for monitoring the quality of engine oil or other nonaqueous media that are installed in vehicles and heavy-equipment, including for example hydraulic systems and vacuum pumps. The present invention provides an affordable and economical means for monitoring the quality of various nonaqueous environments and potentially extending the life of the associated parts. The sensing device is small, lightweight, inexpensive and easy to install so that the device is readily adaptable in existing equipment and vehicles, with or without ECM, and provided as an option with new ECMs.

Other features and advantages of the present invention will be apparent from the following more detailed description of the preferred embodiments, taken in conjunction with the accompanying drawings, which illustrate by way of example, the principles of the invention.

BRIEF DESCRIPTION OF THE DRAWINGS

FIG. 1 illustrates the chemical structure of the conductive polymer polyaniline in the emeraldine base form and the protonated form;

FIG. 8 is a schematic view of the monitoring system of the invention incorporated into an automobile.

DESCRIPTION OF THE PREFERRED EMBODIMENTS

Figure 2:
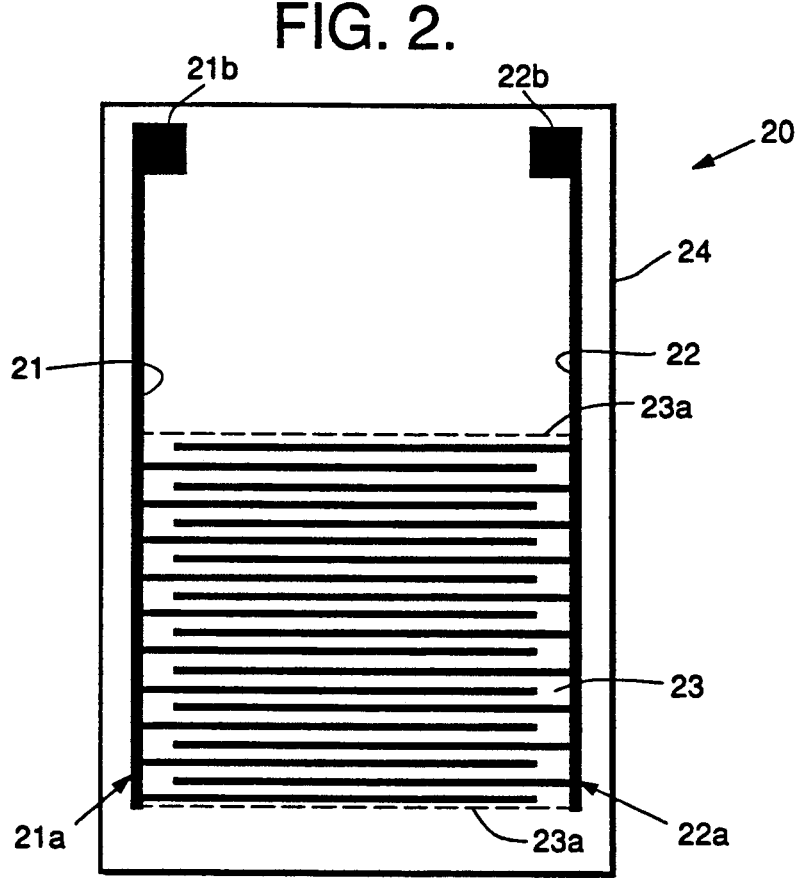
FIG. 2 illustrates a conductive polymer sensor according to the invention.

The sensing device of the present invention is fabricated by depositing electrodes on a substrate in an interdigitated pattern. The substrate material is glass, for example, or another insulating substrate, such as ceramic. The electrode material is an electrically conductive metal, preferably a metal that is not corroded by acids or water, and is not electrochemically active, such as gold. The conductive polymer is deposited on the substrate over the interdigitated electrodes as a thin film. The conductive polymer is deposited until the interdigitated region is completely covered.

The conductive polymer is electrochemically synthesized in a highly conductive state and is converted to an insulating state by neutralization in 10% ammonium hydroxide. It is the conductive polymer in an insulating state which is used to detect acid or water in the nonaqueous media according to the invention. The conductive polymer in the insulating state becomes conductive by protonation with hydrogen ions ($H^+$) of an acid species, or by hydration with water. Acids are degradative products of hydrocarbon-based media, such as motor oil and transmission fluid. They are also products of combustion of the fuel and can collect in the oil from that source. Water is also a product of combustion and often collects in the oil, especially during cold weather and short periods of engine operation. In the latter case, water can condense into the oil from the ambient and will accumulate, if the engine is not operated long enough to evaporate off the water.

The present invention preferably uses polyaniline as the conductive polymer, because polyaniline is unlike other conductive polymers, which derive their conductivity from a charge transfer reaction between the parent polymer and a dopant. Polyaniline has a pristine insulating form which becomes conductive by protonation or hydration. The conductivity of polyaniline is proportional to the degree of protonation or the concentration of protonating species or the degree of hydration or the concentration of the hydrating species in the surrounding medium. Therefore, changes in the conductivity of the polyaniline are readily correlated to the acid content, water content and/or acid content in the presence of water of the medium. The derivatives of polyaniline, such as alkyl- or alkoxy-substituted polyanilines may be used as well, since the conductivity of these derivatives is also due to protonation or hydration. The polyaniline derivatives are less preferred because the conductivity of the polyaniline derivatives, in some cases, is less than the parent polyaniline, and some polyaniline derivatives are somewhat soluble in oil.

FIG. 1 illustrates the emeraldine base or insulating form (11) and the protonated/hydrated form (12) of polyaniline. In the emeraldine base form (11) of polyaniline, there are approximately equal numbers of reduced (13) and oxidized (14) repeat units. When exposed to hydrochloric acid (HCl), the polyaniline becomes fully protonated. The structure of the protonated/hydrated form (12) is believed to consist of equal numbers of the reduced repeat units (13) and diprotonated oxidized repeat units (15), which are protonated to a metallic conducting regime. Polyaniline is a long chain, highly conjugated material. Microscopically, polyaniline forms a highly fibrous morphology. The fibers are generally highly intertwined to yield a macroscopic material resembling a sponge with a high surface area. It is the exposure of the high surface area of polyaniline to the surrounding medium that renders polyaniline so sensitive to changes in the medium.

Moreover, the thermal stability of polyaniline is good. The neutral material shows stability up to 420° C., and the doped or protonated material can show stability up to 250° C., but is somewhat dependent on the chemical structure of the associated anion. Maximum engine temperatures are about 160° C., and such high temperatures are observed only under high stress loads on the engine.

Polyaniline can be deposited as a film cast from solution, or more preferably, prepared by electrochemical polymerization and deposition, as described below. The conductivity of the neutral material can be caused to increase merely by exposing the film to acidic conditions, both in aqueous and nonaqueous, polar media (e.g., acetonitrile). As described herein, the conductivity of the neutral material can also be caused to increase by exposing the film to acidic or wet conditions even in nonpolar media, such as hydrocarbon-based oil. Protonation of polyaniline is effective with both strong acids (i.e., hydrochloric acid) and with weak acids (i.e., acetic acid). This latter effect is important since the acid strength of acetic acid is similar to that of the carboxylic acids formed in the degradation of hydrocarbon-based oil. The hydration of polyaniline can also lead to increased conductivity as a result of proton exchange between the polymer and absorbed water. Moreover, the effect of protonic doping and hydration of polyaniline is reversible. As the protons and/or water are removed from the backbone of polyaniline, the conductivity is reduced back to the insulating form.

More importantly, the source of the conductivity in polyaniline is electronic, not ionic. In other words, the movement of charge through the film is advantageously accomplished by the movement of electrons, not by the migration of ions, as provided in conventional electrochemical devices which measure the concentration of ions present in the medium. This is a key difference in the operation of the sensor according to the invention from that of other electronic acid-measuring devices of the prior art, such as that described by Megerle. Thus, protonation and deprotonation, and subsequent delocalization of the electrons, advantageously control the level of the conductivity and the reversibility of the conductivity. An electrochemical device monitors the deposition or plating of materials at one of the electrodes, which can build up and cause the reversibility of ionically conducting systems to be unreliable.

Another drawback of an electrochemical monitor comes into play if a significant ($>1\%$) amount of water is present in the oil. Ionic degradation species that would be detected by this type of sensor are dissolved in the water and are no longer detected. The sensor of the present invention, advantageously and unexpectedly becomes hydrated by the water in the oil and the observed conductivity increases due to a proton exchange reaction between the partially protonated polyaniline and the water. Although, the mechanism of the invention involves ions, they are ions already existing on the polyaniline backbone; they are not ions present due to an electrochemical reaction, as in the prior art device of Megerle, and the increase in conductivity is due to an electronic process.

A thin film of polyaniline was deposited on the insulating substrate after the interdigitated electrodes were deposited by well-known deposition techniques, such as sputtering. The polyaniline was prepared by well-known methods starting with an aqueous solution containing sulfuric acid (0.6M), sodium hydrogen sulfate (0.5M), and freshly distilled aniline (0.44M, in solution as the anilinium salt), as described by Paul, et al., J. Phys. Chem., Vol. 89, 1441 (1985). The polyaniline was electrochemically prepared with a BAS-100B Electrochemical Analyzer operating in the cyclic voltammetry mode between 0 and 900 mV DC with a sweep rate of 50 mV/sec in a two-compartment cell with the interdigitated electrode as the cathode. All potentials were measured against a standard saturated calomel electrode, with a platinum mesh counterelectrode. Four full cycles were usually employed, which yielded a dark blue-green film about 25 micrometers thick in its fully reduced state. Films are obtainable in the fully oxidized state by operating for 3½ or 4½ cycles, stopping the run at 900 mV. These films were similar in appearance to those obtained above. For the invention, the film is converted to the emeraldine base form from either the fully reduced state or the fully oxidized state. In order to obtain polyaniline in the emeraldine base form for the invention (equal units of oxidized and reduced states), the substrate was removed from the synthesis solution and placed in a solution containing sulfuric acid and sodium hydrogen sulfate of the same concentrations as mentioned above and cycled between 0 and 900 mV DC for 1½ or 2½ full cycles, stopping the run at 400 mV DC. These cycling steps modified the resulting oxidation state of the structure of the polyaniline film to the emeraldine base form.

Polyaniline, prepared in this manner, had deposited on the substrate over the interdigitated electrodes and had grown between gold interdigitated electrodes to completely bridge between adjacent digits. As illustrated in FIG. 2, the sensor (20) comprises an insulating substrate (24) and electrodes (21, 22) with 50 finger or digit pairs (21a, 22a), each 5 millimeters long and 25 micrometers wide, with a 60 micrometer period. Both pairs of digits (21a, 22a) were connected as the anode (not shown) for the deposition process. The synthesis and deposition conditions described above were sufficient to completely bridge the gap between the two sets of digits (21a, 22a) so that they were in effect shorted by the conductive polymer (23) before the neutralization step. The borders of the conductive polymer (23) are shown as dashed-lines (23a) in FIG. 2. Subsequent electrical measurements were carried out by applying a 0.2 V DC potential across the electrodes at end portions (21b, 22b) and measuring the resulting current. Before neutralization, as described below, current readings were generally in the milliamp to tens of milliamps range.

The polyaniline (23) deposited on the device was neutralized in 10% ammonium hydroxide for about 1 hour, thoroughly rinsed with water, and dried under vacuum to change the polyaniline to an insulating form for the sensing device according to the invention. After neutralization, the current readings were in the $10^{-9}$ to $10^{-10}$ amp range.

The sensor (20) according to the invention was immersed in 10 to 20 milliliter portions of a high-grade motor oil (Valvoline, All Climate, 10 W-30, grade SG). Electrical leads were attached to the electrodes at end portions (21b, 22b). A small voltage of 0.2 V DC was applied to the electrodes and the resulting current was measured with either an electrometer or a digital voltmeter. The first current measurements were taken before immersion and after immersion in clean oil. Varying amounts of acetic acid and/or water were added to the oil and thoroughly mixed with a homogenizer. Measurements in the oil sample were taken at temperatures ranging from 30° C. (room temperature) to 100° C. Measurements in the oil mixtures were taken at 100° C.

Table 1 summarizes the conductivity results obtained for sensor (20), and are representative of the invention. Modulation, as referred to in Table 1, is the ratio between the final current reading and the initial current reading after and before the sensor is exposed to the environment described. The results in Table 1 illustrate that the sensor (20) exhibits the greatest change in conductivity when 6% of water and 0–6% acetic acid are added to the oil at 100° C. Moreover, a change in conductivity is observed with oil mixed with water both with and without added acetic acid. The more acid added, the greater the modulation, because the acid protonates the polyaniline causing the sudden increase in the conductivity. Hydration of polyaniline appears to have a less pronounced effect on the conductivity, but does have an effect nonetheless, as summarized in Table 1. This effect is believed to be due to the fact that water is considered a weak acid. Therefore, the sensing device according to the invention can monitor the quality of oil for both acid and water contamination, which is not disclosed or suggested in the prior art devices of Yodice et al. and Maeda et al., described previously.

Also demonstrated in Table 1 is that the sensing device according to the invention advantageously measures the acid content in the oil accurately even in the presence of water. As discussed above, electrochemical-type sensors, as taught by Megerle, are not capable of such measurement. Moreover, this feature of the invention is not disclosed or suggested by Yodice et al. and Maeda et al.

TABLE 1

| TEMPERATURE | WATER | ACETIC ACID | MODULATION |
| --- | --- | --- | --- |
| 30–100° C. | — | — | +200 times |
| 100° C. | 0–6% | — | +10 times |
| 100° C. | 6% | 0–6% | +1000 times |
| 100° C. | 6% | 0–0.5% | +20 times |

Figure 3:
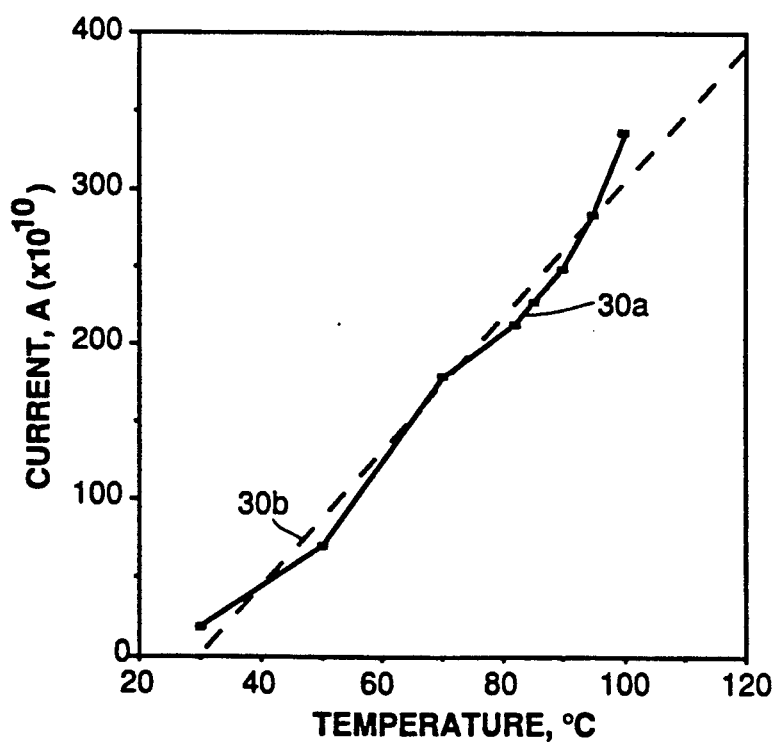
FIG. 3 is a graph illustrating the temperature dependence of a polyaniline-based sensing device between 30° and 100° C. immersed in fresh oil according to the present invention.

FIG. 3 illustrates the behavior of the sensing device according to the invention with temperature when immersed in clean oil (not mixed with contaminants). The solid line (30a) indicates the actual data taken and the dashed-line (30b) is a least squares fit to the data. A linear relationship is illustrated ($r^2 = 0.973$) between the conductivity (measured by current) of the sensor and the temperature so that the influence of temperature can be compensated for in a real environment. The current increases with increasing temperature from 30° C. to 100° C.

Figure 4:
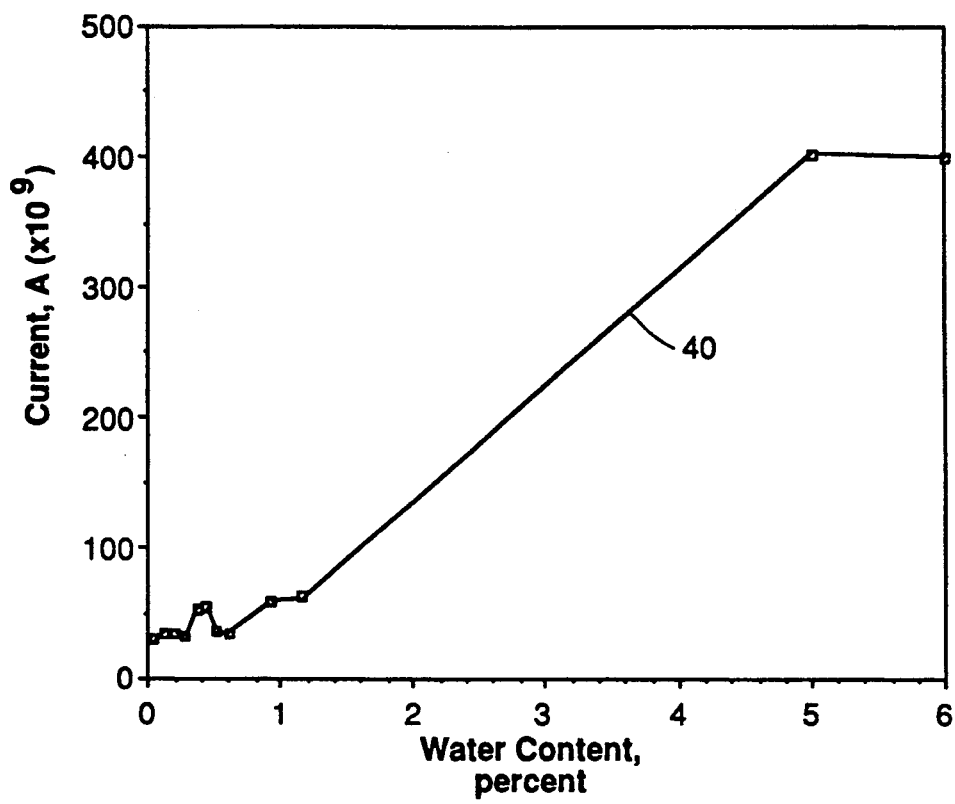
FIG. 4 is a graph illustrating the sensitivity of a polyaniline-based sensing device according to the invention to different concentrations of water in oil at 100° C.

FIG. 4 illustrates the sensitivity of the sensing device according to the invention to water content in oil. The current in amperes between electrodes (21,22) was measured in different percentages of water content at 100° C. and plotted as solid line (40) in FIG. 4. At a water content of between 0% and about 1%, the sensitivity appears low. Above about 1% water in oil at 100° C., the sensitivity increases significantly to about 6% water in oil according to FIG. 4. Generally, it is believed that water levels in oil of 1 to 10% are typical of engine operation in cool climates. Therefore, when the sensor device is used as an acid sensor only, in the 0 to 1% acid content range, any water present at a similar concentration will have little interference with the detection of the acid. Moreover, even at higher concentrations of water, the sensing device according to the invention will detect even low levels of acid. For example, as little as 0.5% acid can be detected in the presence of 6% water in Table 1. Such a small quantity of acid is below the threshold (of approximately 1%) at which time the oil should be changed.

Figure 5:
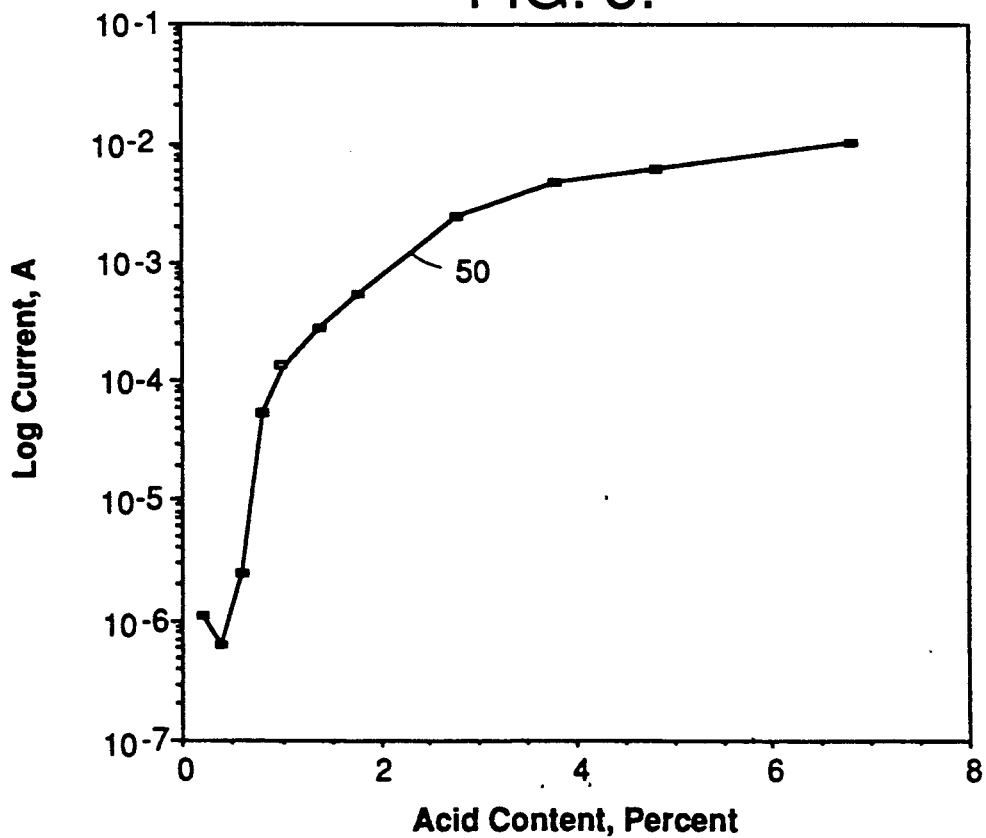
FIG. 5 is a graph illustrating the sensitivity of a polyaniline-based sensing device according to the invention to different concentrations of acid in oil with 6% water present.

FIG. 5 illustrates the sensitivity of the sensor device (20) according to the invention in oil mixed with both acid and water (6%) at 100° C. and further illustrates that acid can be detected even in the presence of water. The logarithm of current was plotted against the percent of acid as solid line 50 in FIG. 5. In the 0% to about 1% range of acid content, the conductivity (current) changes by a factor of about 100, illustrating the greater sensitivity of the sensing device to low concentrations of acid relative to water. This is particularly important in measuring the acid content of motor oil with time and determining when an acid limit has been reached, and therefore, determining in real time when the oil should be replaced.

Figure 6:
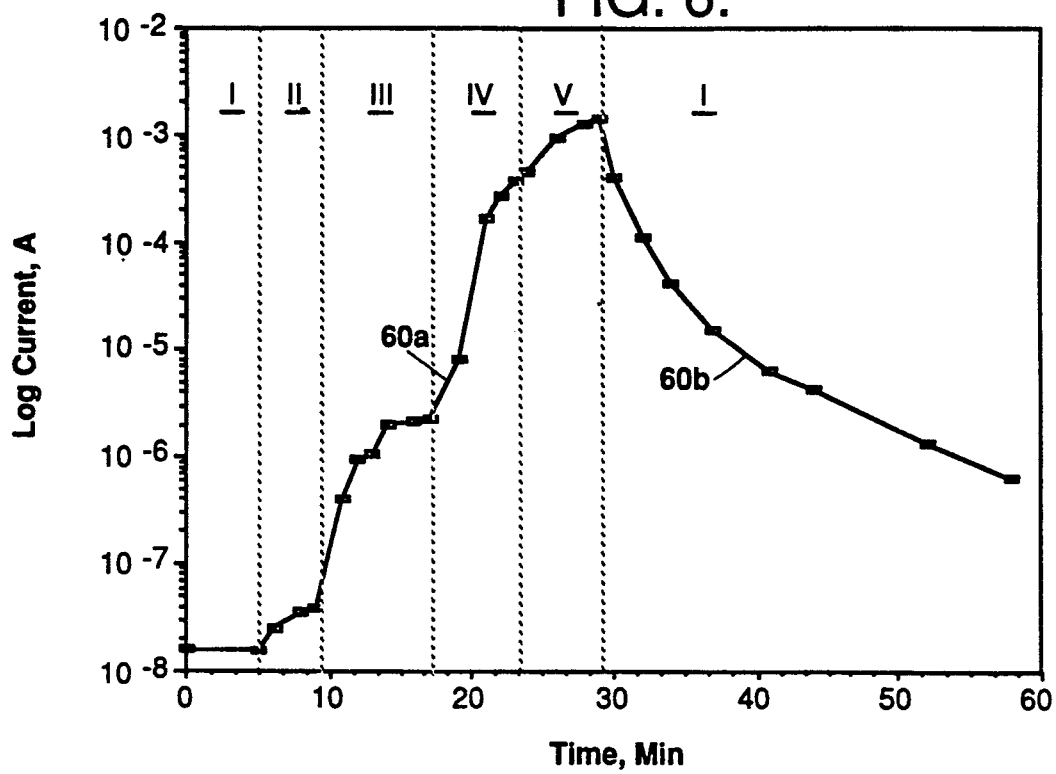
FIG. 6 is a graph illustrating the sensitivity of a polyaniline-based sensing device according to the invention to different concentrations of acetic acid in oil in the absence of water.

FIG. 6 illustrates the sensitivity of the sensing device (20) according to the invention in oil mixed with acid at 100° C. in the absence of water. The device (20) was immersed in oil samples of increasing acid content (samples I-V) as illustrated in dashed-line columnar form in FIG. 6. The acid content in each sample is listed in Table 2. The logarithm of current was plotted against time in minutes as a solid line (60a and 60b) in FIG. 6. Although FIG. 6 illustrates the response of the device (20) plotted against time, it is not intended to illustrate the response time of the sensor device (20). Nonetheless, an indication of response time is illustrated with samples II and III, wherein the current levels tend to reach a maximum over a period of time. FIG. 6 is intended to illustrate that the conductivity (current) increases by over four orders of magnitude between 0 and 3% acetic acid in oil.

TABLE 2

| SAMPLE | PERCENTAGE OF ACETIC ACID |
|---|---|
| I | 0.2 |
| II | 0.6 |
| III | 1.0 |
| IV | 2.0 |
| V | 3.0 |

Also illustrated in FIG. 6 is that the sensing device (20) tends to return to its original state (60b). For example, after exposure to sample V containing 3% acetic acid in oil, the sensing device (20) is reimmersed in the sample I containing 0.2% acetic acid in oil. The conductivity or current changes from about $10^{-3}$ to about $10^{-6}$ amps within about 30 minutes. This is further illustrated in FIG. 7.

Figure 7:
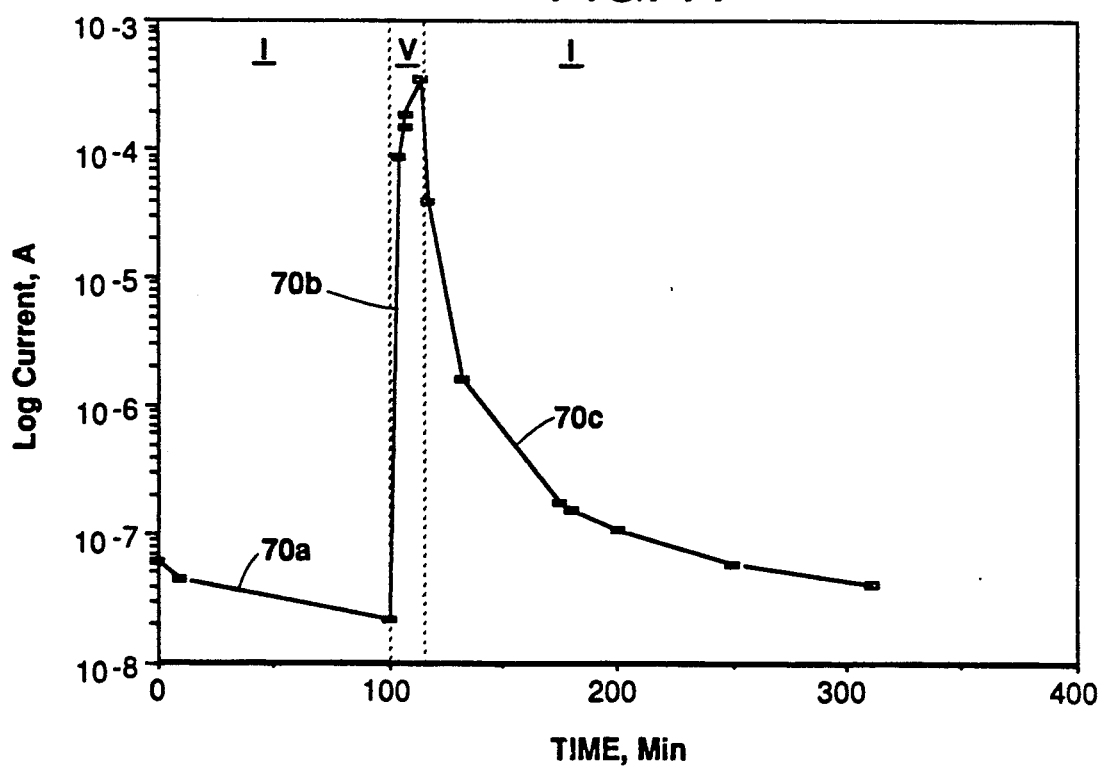
FIG. 7 is a graph illustrating the sensitivity and reversibility of a polyaniline-based sensing device according to the invention to different concentrations of acetic acid in oil at 100° C.

FIG. 7 illustrates the conductivity of the same sensing device (20) immersed in sample I (70a), then sample V (70b), and back to sample I (70c) again, as plotted as the logarithm of current against time in minutes. The data represented the conductivity increases from about $10^{-7}$ amps to about $10^{-3}$ amps and returns to about $10^{-7}$ amps, respectively. Thus, the sensitivity of the sensing device according to the invention is reproducible and the protonation effect is reversible. The recovery time of the sensing device (20) is also exemplified. From an acetic acid concentration of 6% in oil in sample V to the 0.2% acetic acid concentration of sample I, the recovery time was about 190 minutes. In many instances, this recovery time is tolerable, according to the invention, since the time needed for acid build-up as the oil is used and degraded with time is many times longer.

The sensing device (20) is interconnectable to a control means (81) to form a monitoring system (80), as illustrated in FIG. 8 in an automobile, for example, which monitors the acid and/or water content of engine motor oil and provides a warning signal (82) to the operator of the automobile when the acid and/or water content reaches an unacceptable level. The control means (81) can be an existing engine control module (ECM) or a module designed to interface with and process the output of the sensing device (20) according to programmed instructions. The monitoring system (80) according to the invention includes the sensing device (20) welded into the housing which contains the nonaqueous environment to be readily exposed thereto. The device (20) is interconnected to the control means (81) with insulated wires, for example, soldered or welded to the end portions (21b, 22b) of the electrodes (21, 22) at one end and covered with a protective coating and wired into the control means at the opposite end. The control means (81) comprises a minicomputer (not shown) for reading the conductivity of the sensor (20); comparing the conductivity value to a preprogrammed upper limit for the conductivity; and providing an indication to the operator of the equipment of when the upper limit is reached. The control means (81) indicates to the operator that the engine oil or transmission fluid, for example, should be replaced with an audible, or preferably, a visible signal (82). A visible warning signal is preferred so that the signal can remain ON until the fluid replacement is completed. When completed, the sensor (20) automatically reverses back to the insulated form, thereby decreasing the conductivity thereof, and automatically shutting off the warning signal (82). In the case of an automobile or truck, the reversibility of the invention advantageously eliminates the task and the cost of taking the vehicle to the dealer or repair shop to turn OFF or reset the warning light.

Thus, there has been disclosed a sensing device having interdigitated electrodes and a conductive polymer deposited on an insulating substrate for real-time monitoring of the quality of hydrocarbon-based oil and other fluids. The sensing device is based on polyaniline as the active material which is electrodeposited in conductive form and converted to an insulating form that is sensitive to both acid and water, the common components of degraded oil. Changes and modifications may be made to the invention which may be readily apparent to those skilled in the art without going beyond the intended scope of the invention, as defined by the appended claims.

What is claimed is:

1. A device for sensing water content in a nonaqueous medium comprising:
   an insulating substrate;
   interdigitated electrodes deposited on said substrate; and
   an insulating form of a conductive polymer, the conductive polymer deposited over the interdigitated electrodes to bridge between adjacent digits of the electrodes, wherein the insulating form is converted to its conductive form by hydration with the water to provide a current which is proportional to the amount of water and which is measurable.

2. The device for sensing according to claim 1, wherein the conductive polymer is selected from the group consisting of polyaniline and the alkyl- and alkoxy- substituted derivatives of polyaniline.

3. The device for sensing according to claim 1, wherein the conductive polymer is an insulating form of polyaniline.

4. A device for sensing acid content in the presence of water in a nonaqueous medium comprising:
   an insulating substrate;
   interdigitated electrodes deposited on said substrate; and
   an insulating form of a conductive polymer, the conductive polymer deposited over the interdigitated electrodes to bridge between adjacent digits of the electrodes, wherein the insulating form is converted to its conductive form by protonation with the acid and hydration with the water to provide a current which is proportional to the amount of acid and which is measurable.

5. The device for sensing according to claim 4, wherein the conductive polymer is selected from the group consisting of polyaniline and the alkyl- and alkoxy- substituted derivatives of polyaniline.

6. The device for sensing according to claim 4, wherein the conductive polymer is an insulating form of polyaniline.

7. A method of sensing water content and acid content in the presence of water in nonaqueous media comprising the steps of:
   exposing an insulating form of a conductive polymer to a nonaqueous medium, the conductive polymer being deposited over interdigitated electrodes deposited on an insulating substrate, the conductive polymer reversibly increasing conductivity by protonation with the acid and hydration with the water; and
   monitoring the conductivity of said conductive polymer.

8. The method of claim 7, wherein the step of exposing comprises:
   exposing a conductive polymer selected from the group consisting of polyaniline and alkyl- and alkoxy-substituted derivatives of polyaniline deposited on an insulating substrate over interdigitated electrodes; and
   the step of monitoring comprises measuring the conductivity between the interdigitated electrodes.

9. The method of claim 7, wherein the step of exposing comprises exposing an insulating form of polyaniline to the nonaqueous media.

10. A monitoring system for monitoring water content and acid content in the presence of water in nonaqueous media comprising:
    a sensor mounted to be exposed to the nonaqueous media comprising:
      an insulating substrate;
      electrodes formed on the substrate each having an interdigitated portion; and
      an insulating form of a conductive polymer, the conductive polymer deposited over the interdigitated portion of the electrodes as a thin film in an amount sufficient to bridge between adjacent digits, the insulating form being converted to its conductive form by protonation with the acid and hydration with the water in the nonaqueous media to provide a current which is proportional to the amount of acid and to the amount of water and which is measurable;
    control means for measuring the conductivity of the sensor, the control means being capable of indicating when the conductivity reaches a predetermined level;
    warning means for providing an indication when the predetermined level is reached; and
    means for interconnecting the sensor and the warning means to the control means.

11. The monitoring system of claim 10, wherein the conductive polymer is selected from the group consisting of polyaniline and alkyl- and alkoxy-substituted derivatives of polyaniline.

12. The monitoring system of claim 10, wherein the conductive polymer is polyaniline.

13. An automotive monitoring system for monitoring water content and acid content in the presence of water in a nonaqueous medium comprising:
    a sensor mounted to be exposed to the nonaqueous medium comprising:
      an insulating substrate;
      electrodes formed on the substrate each having an interdigitated portion; and
      an insulating form of a conductive polymer, the conductive polymer deposited over the interdigitated portion of the electrodes as a thin film in an amount sufficient to bridge between adjacent digits, the insulating form being converted to its conductive form by protonation with the acid and hydration with the water in the nonaqueous medium to provide a current which is proportional to the amount of acid and to the amount of water and which is measurable;
    control means for measuring the conductivity of the sensor, the control means being capable of indicating when the conductivity reaches a predetermined level;
    warning means for providing an indication when the predetermined level is reached; and
    means for interconnecting the sensor and the warning means to the control means.

14. The automotive monitoring system of claim 13, wherein the conductive polymer is selected from the group consisting of polyaniline and alkyl- and alkoxy-substituted derivatives of polyaniline.

15. The automotive monitoring system of claim 13, wherein the nonaqueous medium is selected from the group consisting of motor oil and transmission fluid, the control means is incorporated into an engine control module (ECM) of the automobile, and wherein the warning means is a visible indicator displayed on a dashboard of the automobile.

16. An automotive sensor for sensing water content in hydrocarbon-based oil and fluid comprising:
    an insulating substrate;
    interdigitated electrodes deposited on said substrate; and
    an insulating form of polyaniline, said polyaniline deposited over the interdigitated electrodes to bridge between adjacent digits of the electrodes, wherein the insulating form of the polyaniline is converted to its conductive form by hydration with the water in the hydrocarbon-based oil and fluid to provide a current which is proportional to the amount of water and which is measurable.

17. An automotive sensor for sensing acid content in the presence of water in hydrocarbon-based oil and fluid comprising:
- an insulating substrate;
- interdigitated electrodes deposited on said substrate; and
- an insulating form of polyaniline deposited over the interdigitated electrodes to bridge between adjacent digits of the electrodes, wherein the insulating form of the polyaniline is converted to its conductive form by protonation with the acid and hydration with the water in the hydrocarbon-based oil and fluid to provide a current which is proportional to the amount of acid and which is measurable.

* * * * *